United States Patent
Gilchrist et al.

(10) Patent No.: US 7,437,984 B2
(45) Date of Patent: Oct. 21, 2008

(54) MICROTOME AND ULTRAMICROTOME WITH IMPROVED CARRIER ARM

(75) Inventors: Raymond T. Gilchrist, Tucson, AZ (US); Leonard J. Ness, Tucson, AZ (US)

(73) Assignee: Boeckeler Instruments Inc., Tucson, AZ (US)

(*) Notice: Subject to any disclaimer, the term of this patent is extended or adjusted under 35 U.S.C. 154(b) by 288 days.

(21) Appl. No.: 11/010,853

(22) Filed: Dec. 10, 2004

(65) Prior Publication Data

US 2006/0123970 A1 Jun. 15, 2006

(51) Int. Cl.
B26D 7/06 (2006.01)

(52) U.S. Cl. .................. 83/703; 83/915.5

(58) Field of Classification Search ........... 83/915.5, 83/703, 704, 708, 410, 879–881, 886, 883, 83/884; 125/13.01, 2; 451/28–31
See application file for complete search history.

(56) References Cited

U.S. PATENT DOCUMENTS

| | | | | |
|---|---|---|---|---|
| 3,828,641 A * | 8/1974 | Sitte | .............................. | 83/703 |
| 3,872,759 A * | 3/1975 | Jackson | ..................... | 83/915.5 |
| 4,051,755 A | 10/1977 | Raveed | | |
| 4,126,069 A * | 11/1978 | Shimonaka | ................. | 83/915.5 |
| 4,269,092 A | 5/1981 | Disharoon | | |
| 4,317,401 A | 3/1982 | Disharoon | | |
| 4,395,075 A * | 7/1983 | Barrett et al. | ............... | 83/915.5 |
| 4,485,706 A | 12/1984 | Disharoon | | |
| 4,511,224 A | 4/1985 | Sitte et al. | | |
| 5,070,935 A * | 12/1991 | Sitte et al. | ...................... | 165/61 |
| 5,161,446 A * | 11/1992 | Holbl et al. | .................... | 83/703 |
| 5,181,443 A | 1/1993 | Sitte et al. | | |
| 5,226,335 A | 7/1993 | Sitte et al. | | |
| 5,282,404 A * | 2/1994 | Leighton et al. | ............ | 83/915.5 |
| 5,299,481 A * | 4/1994 | Lihl et al. | ...................... | 83/170 |
| 5,461,953 A * | 10/1995 | McCormick | ............... | 83/915.5 |
| 5,484,505 A | 1/1996 | Isakson et al. | | |
| 5,522,294 A * | 6/1996 | Krumdieck | ................. | 83/411.1 |
| 5,551,326 A | 9/1996 | Goodman | | |
| 5,609,083 A | 3/1997 | Persson | | |
| 5,752,425 A * | 5/1998 | Asakura et al. | ................ | 83/713 |
| 5,761,977 A * | 6/1998 | Jakobi et al. | ................ | 83/915.5 |
| 5,865,081 A * | 2/1999 | Myers | .......................... | 83/149 |
| 5,906,148 A * | 5/1999 | Aihara et al. | .................... | 83/72 |
| 5,988,029 A * | 11/1999 | Rottermann et al. | ........ | 83/915.5 |
| 6,209,437 B1 * | 4/2001 | Izvoztchikov et al. | ......... | 83/707 |
| 6,568,307 B1 * | 5/2003 | Gunther et al. | ............ | 83/915.5 |
| 6,601,488 B1 * | 8/2003 | Muse et al. | ..................... | 83/13 |
| 6,644,162 B1 | 11/2003 | Temple et al. | | |
| 6,725,673 B1 * | 4/2004 | Rada | ............................. | 62/62 |
| 7,080,583 B2 * | 7/2006 | Lihl et al. | ...................... | 83/13 |

* cited by examiner

Primary Examiner—Jason Prone
(74) Attorney, Agent, or Firm—Mark Ogram

(57) ABSTRACT

A specimen slicing mechanism such as a microtome or an ultramicrotome in which a specimen is held by a specimen arm and is moved through a knife. The specimen arm is made of two segments which are secured to each other via a lockable hinge assembly. The lockable hinge assembly uses a hinge between the two segments as well as a locking mechanism. When locked, the two segments are in a fixed relationship which causes the specimen to be forced through the knife by the action of the motor. When the locking mechanism is unlocked, the segment of the specimen arm holding the specimen is able to rotate ("float") around the hinge; thus allowing the specimen to be sliced by the knife as gravity pulls the segment downward.

15 Claims, 3 Drawing Sheets

MICROTOME AND ULTRAMICROTOME WITH IMPROVED CARRIER ARM

BACKGROUND OF THE INVENTION

This invention relates generally to microtome and ultramicrotome mechanisms and more particularly to the specimen carrier arm thereof.

Microtome mechanisms are well known in the art. Such devices are described in: U.S. Pat. No. 4,317,401, issued on Mar. 2, 1982, to Disharoon and entitled, "Method and Apparatus for Microtomy"; U.S. Pat. No. 4,484,503, issued to Sitte et al. on Nov. 27, 1984, and entitled "Microtome having a Forward-Feed Control System for the Specimen Arm and/or the Knife"; U.S. Pat. No. 5,609,083, issued to Persson on Mar. 11, 1997, and entitled, "Method of and an Apparatus for Sectioning a Specimen"; and, U.S. Pat. No. 6,644,162, issued to Temple et al. on Nov. 11, 2003, and entitled "Microtome"; all of which are incorporated hereinto by reference.

Ultramicrotome mechanisms are also well known in the art and are used for slicing the specimens into finer slices. Such mechanisms are described in: U.S. Pat. No. 4,051,755, issued to Raveed on Oct. 4, 1977, and entitled, "Ultramicrotome and Attachment Therefore"; U.S. Pat. No. 5,181,443, issued to Sitte et al. on Jan. 26, 1993, and entitled, "Device for Controlling the Drive and Forward Feed of Microtomes, particularly Ultramicrotomes"; and, U.S. Pat. No. 5,226,335, issued to Sitte et al. on Jul. 13, 1993, and entitled, "Automatic Initial-Cutting Device for Microtomes, Particularly Ultramicrotomes"; all of which are incorporated hereinto by reference.

In general, there are two types of microtome mechanisms (and by extension, ultramicrotome mechanisms). The two types are differentiated by how the specimen slice is obtained through the performance of the specimen carrier arm.

In the first type of microtome mechanism, the specimen carrier arm is moved in a powered stroke. This is accomplished when a cam motor pulls or pushes the carrier arm (with specimen) through the knife. This assures that the arm cuts completely through the specimen in each rotation of the cam.

In the second type of microtome mechanism, the specimen arm is raised using the cam motor but is allowed to fall through the knife using gravity and the weight of the specimen arm. This type of mechanism allows a much "softer" type of cutting to be performed which is ideal for certain samples.

Often, a laboratory performing microtome operations is required to have both types of microtome mechanisms so that the needs of a particular sample can be effectively addressed. Obviously, this increases the equipment costs for the laboratory.

It is clear an economic advantage can be obtained if a single mechanism were to serve in both fashions.

SUMMARY OF THE INVENTION

The invention is a specimen slicing mechanism such as a microtome or an ultramicrotome in which a specimen is held by a specimen arm which moves the specimen through a knife. In this context, the invention relates to any mechanism which is used to slice specimens. Further, the invention also relates to a replacement arm for existing specimen slicing mechanisms.

The specimen arm is made of two segments. While, in the locked position the preferred embodiment places these two segments in a linear relationship with each other (i.e. their center lines are co-linear), other arrangements (besides co-linear) are also contemplated as those of ordinary skill in the art readily recognize (e.g. curved or bent).

The two segments are secured to each other via a lockable hinge assembly. This lockable hinge assembly permits the operator to select whether the two segments will be in a fixed relationship or can move relative to each other.

The lockable hinge assembly uses a hinge between the two segments. Ideally the hinge is placed on an interior/center portion of the arm; in alternative embodiments, the hinge is located on an exterior portion of the arm. In either case, the two segments to move relative to each other.

Further, the lockable hinge also incorporates the use of a locking mechanism which renders the hinge immoveable; hence, when the locking mechanism is engaged, the two segments are in a rigid relationship to each other.

In this manner the operator is able to select between a "locked" position and an "unlocked" postion. When "locked", the two segments are in a fixed relationship which causes the specimen to be forced through the knife by the action of the motor. In an "unlocked" relationship, the segment holding the specimen is able to rotate around the hinge; thus allowing the specimen to be sliced by the knife as gravity pulls the arm downward.

This allows the operator to use a single mechanism and yet be able to choose between a rigid arm which forces the specimen through the knife and a flexible arm that uses gravity to "softly" move the specimen through the knife.

The invention, together with various embodiments thereof, will be more fully explained by the accompanying drawings and the descriptions thereof.

DRAWINGS IN BRIEF

Figure 3A:
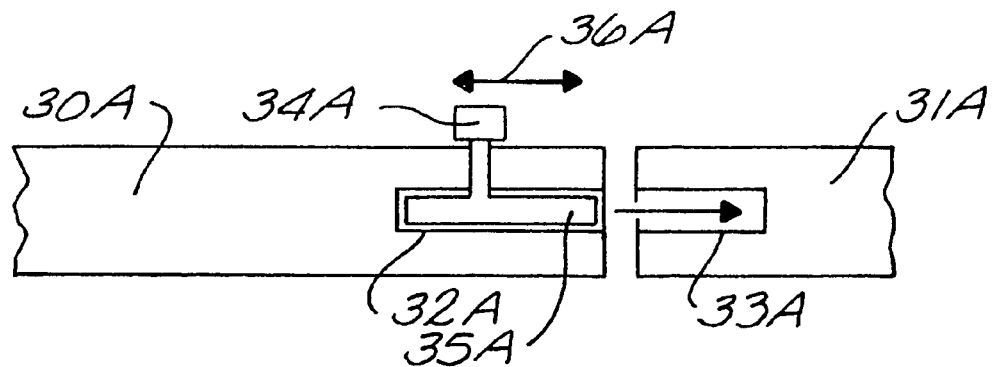
Figure 3B:
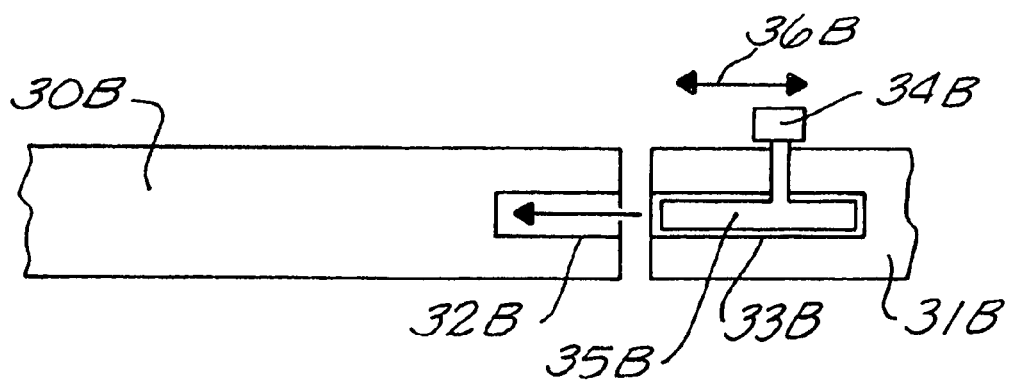
Figure 3C:
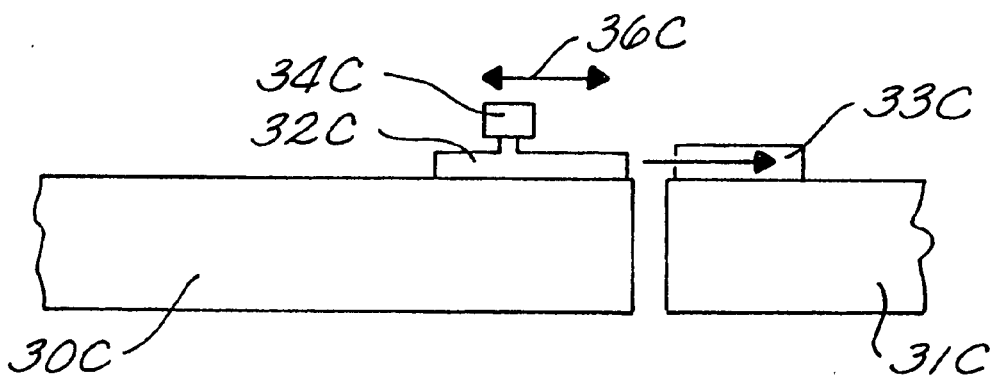

FIGS. 3A, 3B, and 3C are bottom views of the specimen arms and illustrate various mechanisms used to secure the two segments of the specimen arm.

Figure 4A:
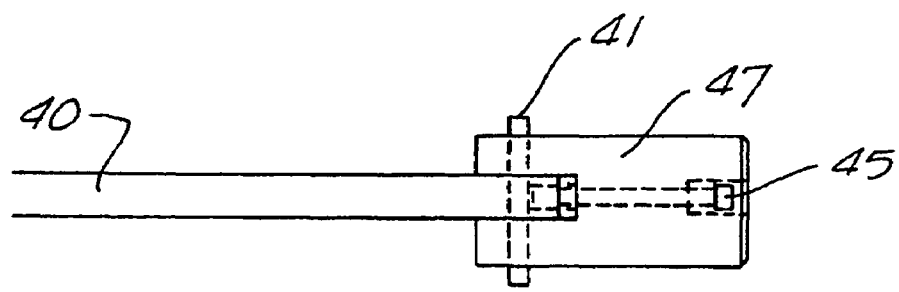
Figure 4B:
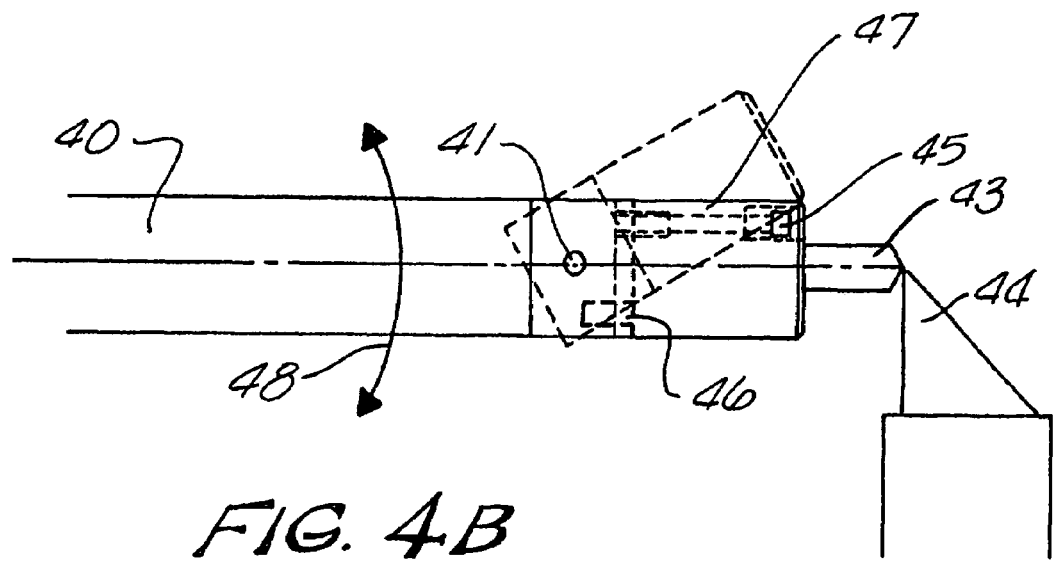

FIGS. 4A and 4B are top and side views of the preferred embodiment of the invention.

DRAWINGS IN DETAIL

Figure 1:
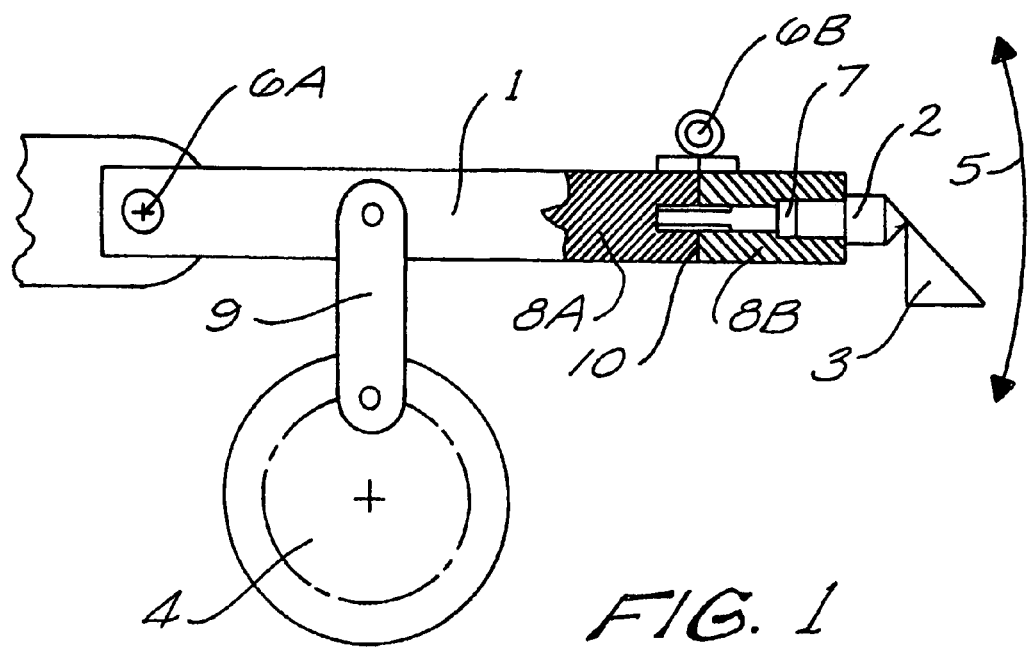
FIG. 1 is a layout of an embodiment of the invention.

FIG. 1 is a layout of an embodiment of the invention.

Specimen arm 1 has segment 8A and segment 8B. Segment 8A is secured at one end to pivot point 6A. Pivot point 6A secures the end of segment 8A relative to motor/cam 4. Motor/cam 4 is secured to a mid-section of segment 8A via connecting rod 9. In this manner, as motor/cam 4 causes connecting rod 9 to move in an up/down motion as indicated by arrows 5, an opposing end 10 of segment 8A of the specimen arm 1 also moves in a like manner.

At end 10 of segment 8A is hinge 6B which secures segment 8A to segment 8B. Specimen 2 is held at one end of segment 8B. As segment 8B moves, specimen 2 is brought into contact with knife 3 which cuts a pre-determined amount from specimen 2.

The motion of segment 8B is defined by the locking mechanism 7. When locking mechanism 7 is in a "locked" state, segment 8A and segment 8B are fixed in a linear relationship; when locking mechanism 7 is in an "unlocked" state, segment 8B is allowed to freely rotate upward as segment 8A is pulled in a downward stroke as powered by motor/cam 4.

The free rotation of segment 8B is caused as specimen 2 comes into contact with knife 3 and resistance to the cutting action is encountered. In this "unlocked" state, the cutting of specimen 2 is accomplished using gravity rather than that powered by the motor; hence a "softer" cutting of the specimen is accomplished.

Figure 2:
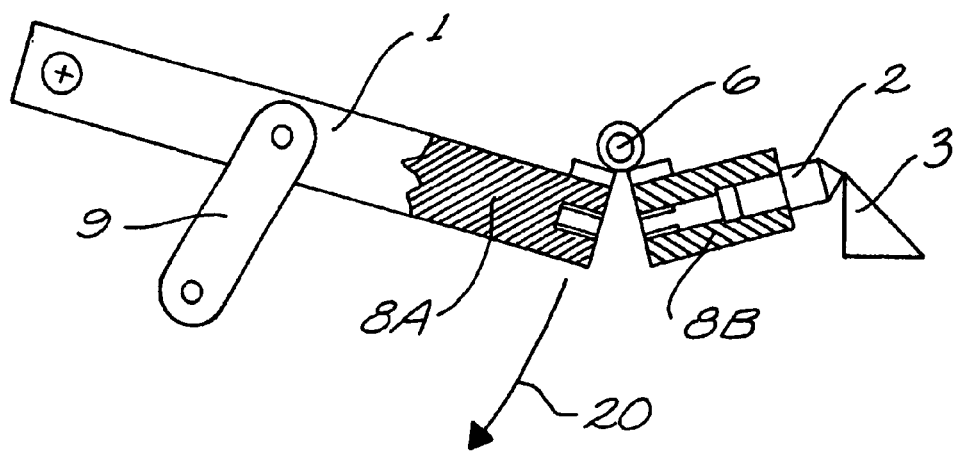
FIG. 2 illustrates the "breaking" of the specimen arm in the preferred embodiment of the invention.

This "softer" or gravity cutting of the specimen is illustrated in FIG. 2. As segment 8A is pulled downward as indicated by arrow 20, segment 8B rotates around hinge 6, allowing gravity to cause the cutting of specimen 2 by knife 3

FIGS. 3A, 3B, and 3C are bottom views of the specimen arms and illustrate various mechanisms used to secure the two segments of the specimen arm.

Referring to FIG. 3A, segment 30A and 31A are secured to each other by a hinge (not shown) located on the upper side segment 30A and segment 31A. Cavity 32A communicates with cavity 33A. Connecting rod 35A is located within cavity 32A and is moved, as illustrated by arrow 36A, by handle 34A (the slide slot to accomondate movement 36A of handle 34A). When connecting rod 35A is extended into cavity 33A, segment 30A and 31A are fixed into a rigid relationship. When connecting rod 35A is pulled back into cavity 32A, then segment 31A is able to rotate about the hinge (not shown in this illustration).

In this manner, the operator is able to select which mode of operation the specimen arm operates within.

Referring to FIG. 3B, segment 30B and 31B form the specimen arm and are secured to each other by a hinge illustrated above. The hinge is located on the upper side segment 30B and segment 31B.

Cavity 32B communicates with cavity 33B. Connecting rod 35B is located within cavity 33B and is moved, as illustrated by arrow 36B, by handle 34B. Again the slide slot to accommodate movement 36B of handle 34B is not shown.

When connecting rod 35B is extended into cavity 33B, segment 30B and 31B are fixed into a rigid relationship. When connecting rod 35B is pulled back into cavity 33B, then segment 31B is able to rotate about the hinge (not shown in this illustration).

Referring now to FIG. 3C, again segment 30C and 31C form the specimen arm. Segment 30C and 31C are secured to each other by a hinge (not shown) located on the upper side segment 30C and segment 31C.

In this embodiment, the locking mechanism is located exterior to segment 30C and segment 31C. Enclosure 32C communicates with cavity 33C. The connecting rod in this illustration is not visible and is contained within enclosure 32C and is moved, as illustrated by arrow 36C, to engage enclosure 33C using handle 34C When connecting rod 35C is extended into enclosure 33C, segment 30C and 31C are fixed into a rigid relationship. When connecting rod 35C is pulled back into enclosure 32C, then segment 31C is able to rotate about the hinge (not shown in this illustration).

In this manner, the operator is able to select which mode of operation the specimen arm operates within.

FIGS. 4A and 4B are top and side views respectively of the preferred embodiment of the invention.

Arm 40 is secured to extension arm 47 via pivot 41. In this manner, as arm 40 is moved as indicated by arrow 48, extension arm 47 is able to move as specimen 43 engages knife 44.

In this embodiment, extension arm 47 is "locked" into a rigid relationship with arm 40 when locking bolt 45 is screwed through extension arm 47 to engage a forward face of arm 40. This engagement, along with the engagement of adjustment bolt 46, creates a firm securement of extension arm 47 with arm 40 so that the mechanism works as a rigid arm mechanism.

It is clear from the foregoing, the present invention creates a highly improved microtome and ultramicrotome.

What is claimed is:

1. A microtome specimen arm comprising:
   a) a first segment connectable to a motor within a microtome so that, when installed and said motor is operating, said first segment is moved in an up and down motion;
   b) a second segment adapted to hold a specimen at a first end thereof; and,
   c) a hinge assembly member having,
      1) a hinge secured to an upper portion of the first segment and the second segment such that during motion of said first segment, said second segment is free to move relative thereto, and,
      2) a locking mechanism adapted to selectively secure said first segment to said second segment, said locking mechanism including a slide bar selectively engaging both said first segment and said second segment.

2. The microtome specimen arm according to claim 1, wherein said slide bar is enclosed within said first segment of said specimen arm and wherein a portion of said slide bar is moveable into an opening within said second segment.

3. The microtome specimen arm according to claim 1, wherein said slide bar is enclosed within said second segment of said specimen arm and wherein a portion of said slide bar is moveable into an opening within said first segment of said specimen arm.

4. The microtome specimen arm according to claim 1, wherein said slide bar is positioned exterior to said first segment and said second segment.

5. A microtome mechanism comprising:
   a) a knife;
   b) a specimen arm having a first segment and a second segment, said first segment being moved in an up and down motion, and wherein a first end of said second segment is secured by a hinge assembly to a first end of said first segment such that during motion of said first segment, said second segment is free to move relative to said first segment, a second end of said second segment being positioned proximate to said knife and adapted to hold a specimen; and,
   c) a locking mechanism having a slide bar selectively engaging said first and second segments and configured such that,
      1) when said locking mechanism is locked, said first segment and said second segment remain in a fixed relationship, and,
      2) when said locking mechanism is unlocked, said second segment is permitted to rotate about said hinge assembly.

6. The microtome mechanism according to claim 5, wherein said slid bar is enclosed within said first segment of said specimen arm and wherein a portion of said slide bar is moveable into an opening within said second segment arm.

7. The microtome mechanism according to claim 5, wherein said slide bar is enclosed within said second segment of said specimen arm and where a portion of said slide bar is moveable into an opening within said first segment of said specimen arm.

8. The microtome mechanism according to claim 5, wherein said slide bar is positioned exterior to said first segment and said second segment of said specimen arm.

9. The microtome mechanism according to claim 5,
   a) further including a motor powering a cam mechanism; and,
   b) wherein the first segment of said specimen arm is moved in said up and down motion by motion of said cam mechanism.

10. The microtome mechanism according to claim 9, wherein a second end of said first segment is permanently affixed relative to said motor and said cam mechanism.

11. The microtome mechanism according to claim 10, wherein said cam mechanism is permanently connected to a point between a first end and a second end of said first segment of said specimen arm.

12. A specimen slicing mechanism comprising:
 a) a knife;
 b) a specimen arm having a first segment and a second segment, said first segment being movable in an up and down motion, and wherein a first end of said second segment is secured by a hinge assembly to a first end of said first segment, said hinge assembly permitting motion between said first segment and said second segment during motion of said first segment, a second end of said second segment being positioned proximate to said knife and adapted to hold a specimen;
 c) a motor powering a cam mechanism, wherein the first segment of said specimen arm is moved in said up and down motion in response to motion of said cam mechanism;
 d) wherein a second end of said first segment is permanently affixed relative to said motor and said cam mechanism; and,
 e) a locking mechanism having a slide bar selectively engaging said first and second segments and configured such that,
  1) when said locking mechanism is locked, said first segment and said second segment remain in a fixed relationship, and,
  2) when said locking mechanism is unlocked, said second segment is permitted to rotate around said hinge assembly.

13. The specimen slicing mechanism according to claim 12, wherein said slide bar is enclosed within said first segment of said specimen arm and wherein a portion of said slide bar is moveable into an opening within said second segment arm.

14. The specimen slicing mechanism according to claim 12, wherein said slide bar is enclosed within said second segment of said specimen arm and wherein a portion of said slide bar is moveable into an opening within said first segment of said specimen arm.

15. The specimen slicing mechanism according to claim 12, wherein said slide bar is positioned exterior to said first segment and said second segment of said specimen arm.

* * * * *